United States Patent [19]

Pflug

[11] 3,960,670
[45] June 1, 1976

[54] METHOD AND APPARATUS FOR STERILITY MONITORING

[76] Inventor: Irving J. Pflug, 10 E. Oaks, St. Paul, Minn. 55110

[22] Filed: Sept. 2, 1975

[21] Appl. No.: 609,700

[52] U.S. Cl. .............................. 195/103.5 R; 21/56; 21/92; 21/93; 21/94; 21/103; 195/54; 195/139
[51] Int. Cl.² .......................................... C12K 1/04
[58] Field of Search ............... 195/54, 103.5 R, 127, 195/139; 21/56, 92–95, 96, 97, 98, 103; 426/231, 232

[56] References Cited

UNITED STATES PATENTS

| | | | |
|---|---|---|---|
| 2,854,384 | 9/1958 | Beckley et al. | 195/54 |
| 3,239,429 | 3/1966 | Menoplasino et al. | 195/103.5 R |
| 3,346,464 | 10/1967 | Ernst | 195/103.5 R |
| 3,440,144 | 4/1969 | Andersen | 195/103.5 R |
| 3,661,717 | 5/1972 | Nelson | 195/103.5 R |

*Primary Examiner*—A. Louis Monacell
*Assistant Examiner*—Robert J. Warden
*Attorney, Agent, or Firm*—Stephen D. Carver

[57] ABSTRACT

A method and apparatus for monitoring the effectiveness of a sterilization cycle of a product that is sterilized inside a container are provided. The apparatus comprises an elongated, preferably plastic rod which is designed to extend interiorly of a container into the center or most difficult point to sterilize in the contents thereof, a reservoir located internally of the rod for receiving a sterilization sensitive agent, a means for hermetically sealing the reservoir to isolate the sterilization-sensitive agent from the contents of the container, and a mechanical means for rigidly attaching or fastening the rod to the container. The container which will usually be filled with a food or drug product, may be of conventional construction, such as a metallic can, glass or plastic bottle, or flexible package. The length of the rod is chosen such that the internal reservoir will be positioned within the slowest heating zone within the container. The method disclosed herein comprises the steps of hermetically sealing a predetermined quantity of a sterilization-sensitive agent within a reservoir provided in a rod, rigidly fastening the rod to an end of the container whereby the rod extends interiorly of the container and is rigidly positioned there within during the sterilization process, conventionally filling the container with food or the like and sealing same, subjecting the container to the sterilization cycle to be monitored, and subsequently analyzing the sterilization-sensitive agent to determine the effects of the sterilization process just completed. The sterilization-sensitive agent preferably employed comprises a viable bacteria in a liquid suspending menstrum. A sterilization-sensitive chemical such as thiamine hydrochloride can also be used.

10 Claims, 5 Drawing Figures

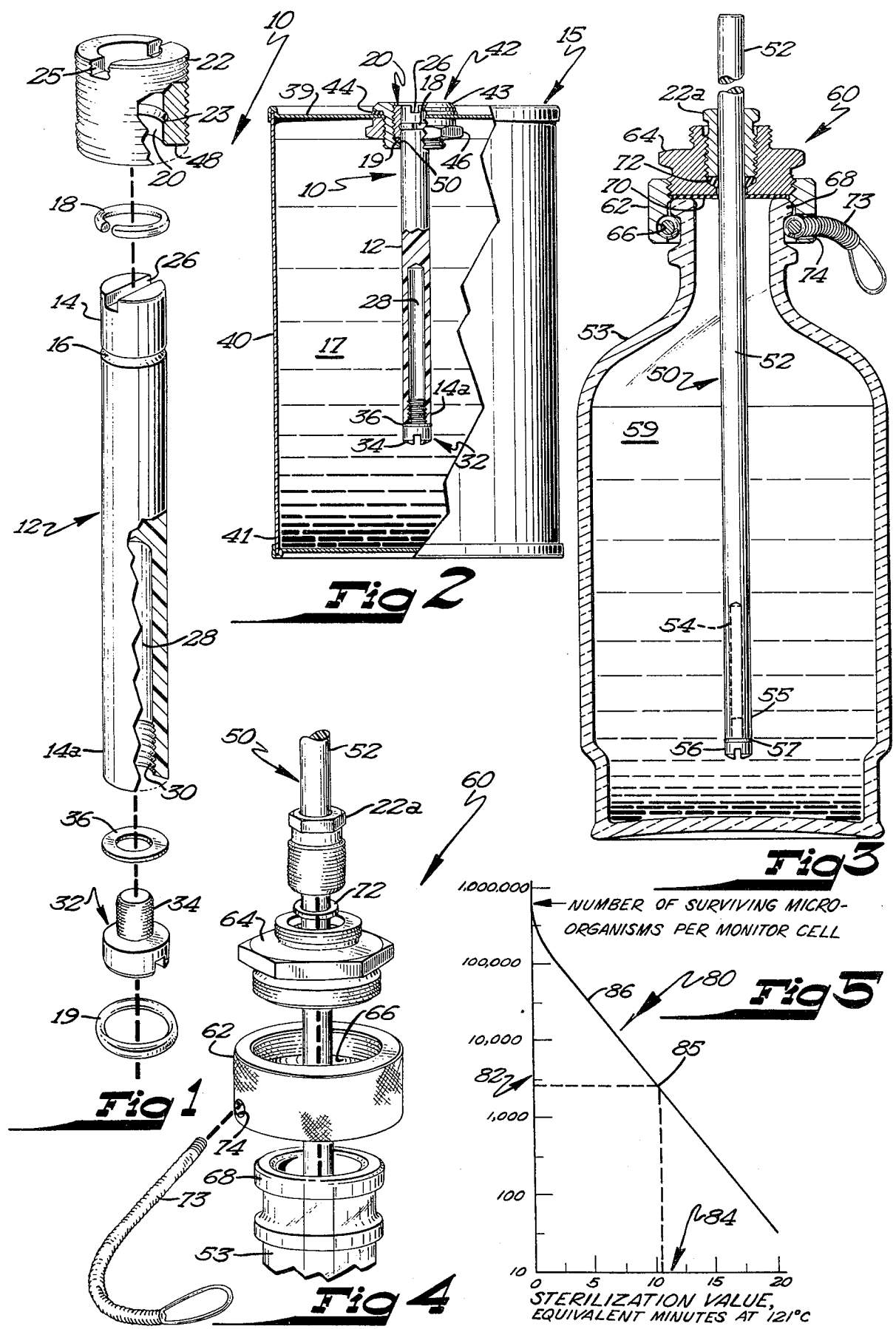

METHOD AND APPARATUS FOR STERILITY MONITORING

BACKGROUND OF THE INVENTION

This invention relates generally to sterilization processes. More particularly, this invention relates to a method and apparatus for monitoring or determining the effectiveness of a serilization process on a product that is sterilized inside a hermetic container.

In general, the concept of sterilization involves the elimination or at least the minimization of unwanted biological organisms from a particular environment. Food and drug products in containers, for example, may be sterilized by subjecting the containers to a heat sterilization process. In heat sterilization it is the high temperature acting over a period of time that results in the death of the unwanted biological contamination. Measuring temperature alone will not indicate the killing power of the sterilization treatment on bacteria; it is necessary to integrate the time and temperature of treatment. In the canned food industry, the sterilization cycle usually involves the use of steam to heat properly filled, sealed containers. To be effective, the sterilization process must function adequately even in the slowest heating zone of the container.

A widely used approach to the monitoring of sterilization processes employs bacterial spores. When a predetermined number of spores are subjected to the sterilization agent, death of the spores will proceed in a predictable manner. When the sterilization process is completed, a certain percentage of the test spores will have been killed depending on the severity of the treatment, the remainder will still be alive. When the surviving number of test bacteria is subsequently determined (through a variety of conventional techniques), a reasonable measure of the severity of the particular sterilization process will be obtained. This method of monitoring sterilization processes of course assumes that the death rate of microorganisms within the container will be approximately the same as the death rate experienced by the test biological organisms.

In the prior art, a variety of bacterial sterility process monitoring systems are known. One general group of such systems specifically for use in hospital autoclaves employs a predetermined number of viable microorganisms deposited on a piece of filter paper. The paper strips in envelopes may be used alone, or in one system, an adjacent cell containing a food or life sustaining substance separated by one or more reinforcing membranes or walls all in a compartment together. In this latter system the apparatus is subjected to the sterility process to be investigated, and afterwards withdrawn and manually crushed so that the bacteria or other microorganisms therewithin are fed by the nutrient medium enclosed in a vial. Detector material provided may subsequently indicate the effectiveness of the sterilization cycle in response to microorganism growth therewithin. Examples of systems of the above types include U.S. Pats. No. 3,611,717, issued May 9, 1972, U.S. Pat. No. 3,440,144 issued Apr. 22, 1969, U.S. Pat. No. 3,346,464, issued Oct. 10, 1967, U.S. Pat. No. 3,239,429, issued on Mar. 8, 1966, and U.S. Pat. No. 3,854,384 issued on Sept. 30, 1958. Each of the preceding patents discloses a sterilization monitor apparatus which may be subjected to the sterilization process along with the material to be sterilized. However, none of these preceding references disclose a means for rigidly positioning the apparatus within the critical slow-heating zone within a container to be sterilized or for isolating the sterilization-sensitive material completely and hermetically from either the product being sterilized or the heating medium that is acting as the sterilization agent. An example of the sterilization indicator system which employs chemicals rather than microorganisms or other life forms is seen in U.S. Pat. No. 3,627,469 issued on Dec. 14, 1971. The latter reference discloses a plurality of sterilization indicators which function by means of a change in color, depending upon the effectiveness of the sterilization cycle.

One of the biggest problems experienced with the use of microorganism or bacterial sterility indicators has been the ambiguity of the results achieved therefrom. Some prior art devices indicate only that bacteria have or have not survived the sterilization process. Moreover, it is difficult to ascertain what section of a container, for example, experienced the same heating effects as did the monitor cells employed. As mentioned, some of these prior art monitor cells are adapted to be manually squeezed after the cycle to free the nutrient medium so it can mix with the surviving microorganisms. While this factor may be desirable in certain circumstances, in a mechanized sterilization process where a vast quantity of cans or bottles, for example, must be sterilized, such systems are simply too structurally unsound to provide adequate or dependable results. Most prior art monitors are designed so that the heating medium comes in contact with the heat-sensitive agent during the sterilization cycle. Contact between the heating medium and the heatsensitive agent may be acceptable when steam is the heating medium; however, contact between any other heating medium or product and the sensitive agent may change the calibration of the sensitive agent and give erroneous results. Another problem with prior art sterilization monitors is that wires or leads are often required. This is true in the case of conventional thermocouples. When such lead wires are required, the object being tested often cannot be subjected to the sterilization process that is actually used in practice because of the complex path that the container must follow in proceeding through the sterilization equipment.

SUMMARY OF THE INVENTION

Briefly described, the apparatus disclosed herein comprises an elongated, preferably plastic tube or rod which includes an inner reservoir for containing microorganisms or other heat-sensitive agent. Means are provided to hermetically seal the reservoir so that the bacteria or other test microorganism or chemical inserted therewithin are hermetically sealed and prevented from contacting the contents of the container being tested. Importantly, mechanical attachment means are provided for rigidly fastening the rod to an end of the container, whereby the internal reservoir is positioned substantially within the slowest heating zone within the container being sterilized. The very durable and substantially rigid apparatus can be fastened to a can, for example, without the use of lead wires or the like, so that the container can be mechanically processed through continuous agitating type sterilization cycle in the normal manner. In other words, no modifications are necessary to the sterilization apparatus and reliable practical results may be achieved with the described apparatus.

The method disclosed herein briefly comprises the steps of hermetically sealing a predetermined quantity of a heat-sensitive agent within a reservoir or cell, locating the cell interiorly at the slowest heating zone in a container, filling the container and sealing it in the normal manner, and subjecting the container to the conventional sterilization process. The microorganism-bearing reservoir is positioned interiorly of an elongated rod, and the construction of the rod enables the reservoir to be appropriately placed within the slowest heating zone within the container to be sterilized. After the sterilization process is completed, the microorganism content within the reservoir is determined through conventional quantitative techniques, thereby indicating the effectiveness of the sterilization cycle.

Thus, a primary object of this invention is to provide a method and apparatus for efficiently monitoring sterilization processes.

It is a further object of this invention to provide sterilization monitoring apparatus of the character described which will serve as a receptacle for the heat-sensitive solution such as chemical compounds or bacterial spores or other microorganisms.

A further object of this invention is to provide a sterilization monitor which will isolate the heat-sensitive agent employed therein from the product in the container being sterilized or from the heating medium used in the system. It is a feature of this invention that the reservoir is hermetically sealed to prevent intermingling of the heat-sensitive agent with the contents of the container in which the apparatus is mounted, or vice versa.

Another object of this invention is to provide a sterilization monitoring system which will positively and rigidly maintain the calibrated sterilization monitoring material within the slowest heating zone in the container.

Still another object of this invention is to provide a sterilization monitoring system which will function adequately without the use of connecting electrodes or other wires or terminals. It is a feature of this invention that the sterilization monitor apparatus can be attached to the container being sterilized simply by fastening a threaded fitting on an end of the container and the container processed in the normal manner no matter what processing method is used.

Yet another object of this invention is to provide a sterilization monitoring apparatus of the character described above which will withstand the high temperatures and pressures generated during the sterilization of a container having food contents or drug products therein.

A related object of this invention is to provide a method for monitoring sterilization processes and for determining the efficacy thereof.

These and other objects of this invention along with features of novelty appurtenant thereto, will appear or become apparent in the course of the following description.

BRIEF DESCRIPTION OF THE DRAWINGS

In the following drawings, which form a part of the specification and are to be construed in conjunction therewith, and in which like reference numerals have been employed to indicate like parts in the various views;

FIG. 1 is an enlarged, exploded perspective view of a sterilization monitor cell constructed in accordance with the teachings of this invention, with parts thereof broken away or shown in section for clarity;

FIG. 2 is a cross sectional view showing the monitor cell installed within a can or similar container which is to be subjected to a sterilization process;

FIG. 3 is a cross sectional view showing an alternative embodiment of the invention installed in bottle of parenteral solution which is to be subjected to a sterilization process;

FIG. 4 is a perspective view of the apparatus shown in FIG. 3; and

FIG. 5 shows a graphical calibration chart for determining the effectiveness of the sterilization process.

DETAILED DESCRIPTION

Referring initially to FIGS. 1 and 2 of the drawings, a sterilization monitor cell 10 is there shown. Monitor cell 10 preferably comprises an elongated, cylindrical rod portion 12 which is adapted to be attached to a container. As will be described in more detail, the length of rod 12 will be dependent upon the size or dimensions of the container with which it will be used. In the preferred embodiment rod 12 will be comprised of plastic such as nylon or the like. Rod 12 includes an upper end 14 which will be rigidly attached to one end of the container 15 in which the rod will be mounted and a lower end 14A which will extend interiorally of container 15 into heat exchange relationship with the contents 17 therewithin.

Upper end 14 includes a circumferential groove 16 which is adapted to receive a circular snap ring 18. A gasket 19 will be positioned below groove 16. When ring 18 is appropriately placed within groove 16, rod end 14 will be actually extended into the interior 20 of a threaded nut or fitting 22. Ring 18 is thus matingly fitted within an internal, circumferential groove 23 provided in fitting 22, so that axial displacement between rod 12 and fitting 22 will be prevented. Additionally, O-ring 19 will provide a fluid-tight seal between fitting 22 and rod 12 so that the contents of the container cannot escape during the sterilization process.

Nut 22 includes a transverse channel 25 for manipulation thereof by a screwdriver or the like. When assembled, an optional upper transverse channel 26 provided in end 14 of the rod 12 will parallel channel 25 so that a screwdriver may be used for assembly. Of course, it will be apparent that channels 25 and 26 may be omitted where desired.

Although in the preferred embodiment rod 12 is of generally solid construction, lower end 14A includes a hallowed internal reservoir portion 28 which is adapted to receive a sterilization sensitive agent. Reservoir 28 is in fluid flow communication with a generally tubular, internally threaded portion 30 which is adapted to matingly receive a closure means 32. Closure means 32 preferably comprises a threaded capscrew 34 which is adapted to be threadably received within orifice 30. A preferably rubber or plastic gasket 36 is included to provide a hermetic seal when the capscrew 34 is tightened within orifice 30 such that the contents of the internal reservoir 28 are isolated from the contents of the container. During the manufacture of the rod 12 reservoir 28 is first formed through drilling or the like, and passageway 30 is then tapped or threaded.

In FIG. 2 the apparatus 10 is shown installed within the conventional, metallic container 15. Container 15 includes an upper end portion 39 which is attached to the conventional cylindrical body portion 40 in a conventional manner. An attachment fitting 42 is provided as a center of can end 39 for rigidly positioning the apparatus 10. Fitting 42 includes a generally T-shaped, tubular, threaded portion 43, a circular sealing gasket 44, and a threaded nut 46 which compressably and threadably engages portion 43 to rigidly secure the fitting. Apparatus 10 is rigidly attached to fitting 42 by threadably mating fitting 22 internally of threaded position 43. A seal is provided when the lower oblique shoulder portion 48 of fitting 22 engages O-ring 19 against a lower tapered shoulder portion 50 provided internally of fitting portion 43. Packing nut 22, and fitting 42 thus function as an attachment means. Fitting 42 is a conventional item obtainable from the O. F. Ecklund Company in Cape Coral, Florida and is designated as receptor "C5".

The length of rod 12 is chosen such that the internal reservoir portion 28 therewithin will be positioned in the slowest heating zone within the container in which the apparatus is installed. Normally the slowest heating zone will be in the geometric center of the container being sterilized. Where non-symmetrical container shapes are encountered, however, the slowest heatng zone must be at first ascertained by consulting the supplier or manufacture of the said device or container, and the length of the rod 12 should be adjusted accordingly.

With reference now to FIGS. 3 and 4, a slightly modified monitor cell 50 for use with a glass bottle or container as shown. More particularly, apparatus 50 is adapted for use with a parenteral bottle 53 of the type conventionally employed in the medical arts. Similarly, apparatus 50 comprises a generally cylindrical rod 52 which has an internal reservoir portion 54 provided at the lower end 55 thereof. In the preferred embodiment reservoir 54 is hermetically sealed by capscrew 56 which is matingly received within a threaded aperture at the bottom of the reservoir 54. A sealing gasket 57 is likewise provided. When cap 56 is tightly received within rod end 55 the reservoir portion 54 will be hermetically sealed from the contents 59 of the container 52, so that the heat sensitive agent within the reservoir will be isolated from the contents of the bottle or container and vice versa.

A fitting means 60 is provided to rigidly fasten the rod 52 to the container 53. Apparatus 60 is a conventional fitting available from the O. F. Ecklund Company and identified by their catalog number C-18. Apparatus 60 comprises a lower fitting 62, and an intermediate fitting 64 which threadably engages fitting 62. A conventional packing nut 22A threadably and coaxially engages portion 64. As best seen in FIG. 3, fitting member 62 includes an inner circumferential groove 66 which, when apparatus 62 is appropriately placed at the top of the container 53, will be positioned immediately below an upper circumferential flanged lip portion 68 provided at the top of container 53. A conventional flexible wire 73 is adapted to be inserted through a passageway 74 into groove 66 in abutment with lip 68 to rigidly fasten portion 62 to the bottle 53. Afterwards, threaded fitting 64 will be tightly matted with portion 62, and a seal will be provided between portions 64 and 68 by a gasket 70 provided therebetween. Rod 52, which coaxially extends through the fitting apparatus, will be held in place by compression from packing nut 22A and a lower internal gasket 72. Before tightening nut 22A, the rod 52 can be axially positioned within the bottle such that its internal reservoir portion 54 will be appropriately positioned within the slowest heating zone of the bottle. When the apparatus is suitably fastened the container may be subjected to the sterilization process which is to be tested.

The internal reservoir portions of the sterilization monitor cells depicted in FIGS. 1 through 4 are adapted to receive a heat sensitive sterilization agent. The heat sensitive agent preferably employed comprises viable bacteria in a liquid suspending menstrum. One heat sensitive agent suitable for use with the apparatus comprises a population of bacillus stearothermophilus. One convenient source of the aforementioned bacteria is the American Sterilizer Company, in Erie, Pennsylvania. Alternatively, a sterilization sensitive chemical such as Thiamine Hydrochloride can be used. In either case a pre-determined quantity of the sterilization sensitive agent is inserted within the reservoir portion of the rod, and the closure apparatus is tightened to provide a hermetic seal as previously described.

When employing the apparatus 10 in conjunction with a can 15 (FIG. 2) the apparatus is first attached to end 39 of the can as previously described. Subsequently, the can 15 is filled through a conventional process with a food or other material to be sterilized, and the lower end 41 of the can is then attached in any conventional manner. The can may then be subjected to the sterilization process without the use of external wires or other inconvenient attaching devices. In the case of apparatus 50 the bottle 53 must first of course be filled with the solution or contents to be sterilized.

After the sterilization cycle is completed the respective container (15 or 53) is withdrawn and the sterilization monitor cell removed therefrom. The remaining heat sensitive or sterilization sensitive agent in reserves 28 or 54 is then tested to determine the effects of the sterilization cycle thereon. Since the reservoir portions of the rod are positioned within the slowest heating zone within the contents of respective container, analysis of the contents of the reservoir will give an indication of the sterilization experienced in the most difficult area to sterilize in the container.

The effectiveness of the sterilization process may be determined graphically. Referring now to FIG. 5, a graph 80 includes a logarithmically calibrated vertical axis 82 and a horizontal axis 84. Axis 82, for example, indicates the number of surviving micro-organisms remaining in the reservoir after the sterilization process has been completed. Horizontal axis 84 indicates the sterilization value, in minutes. For example, each point along axis 84 indicates a sterilization value which is the equivalent number of minutes at 121° centigrade at which a given number of bacteria will remain. The calibration graph segment 86 is provided by the manufacturer or supplier of the micro-organisms, or it may be determined experimentally through conventional techniques. Thus, after the sterilization process is completed, the number of remaining bacteria are determined conventionally, and the resultant number is entered on the graph. By way of example, an intersection point 85 along graphical segment 86 occurs when 1500 surviving microorganisms are obtained. By translating point 85 along axis 84, it is seen that a sterilization value of 10.5 minutes has been determined. This means that the sterilization process which has been tested provides a sterilization value (or F value as will be recognized by those skilled in the art) of 10.5 minutes at 121° centigrade. Graphical segment 86 is of course dependent upon the microorganism, suspending medium and the calibration temperature, which in this case is 121° centrigrade. Where the graph segment 86 is not known, it may be determined by subjecting prepared monitor cells to sterilizaion processes at several known sterilization values and plotting the numbers of surviving organisms vs. the sterilization value.

While a preferred embodiment of the present invention has been described, it should be understood that various changes, adaptations and modifications may be made therein without departing from the spirit of the invention and the scope of the appended claims.

What is claimed:

1. Apparatus for monitoring the effectiveness of a sterilization cycle on the contents of a container, said apparatus comprising:
    an elongated rod portion adapted to extend interiorly of said container into the contents thereof;
    said rod including an internal reservoir portion adapted to receive a sterilization sensitive agent;
    closure means for hermetically sealing said reservoir portion thereby isolating said heatsensitive agent from said container contents; and
    attachment means for rigidly fastening said apparatus to said container, said attachment means adapted to maintain said container in a sealed condition, and operable to positively maintain said rod in a predetermined position within said container.

2. The combination as in claim 1 wherein said rod includes a generally tubular first end portion in fluid flow communication with said reservoir.

3. The combination as in claim 2 wherein said first rod end portion is internally threaded, and said closure means comprises a cap screw for threadably engaging said first end portion and a gasket sandwiched between said cap screw and said first end portion, whereby said reservoir is hermetically sealed in response to selective tightening of said cap screw.

4. The combination as in claim 3 wherein said rod comprises a generally cylindrical second end portion and said attachment means comprises:
    threaded fitting means for compressively, sealably engaging an end portion of said container through an opening provided in said container end portion; and nut means fastened to said second rod end portion for threadably engaging said fitting means.

5. The combination as in claim 4 including snap ring means associated with said second rod end portion for rigidly engaging said nut means.

6. A method for quantitatively measuring the effectiveness of a sterilization cycle on the contents of a container, said method comprising the steps of:
    hermetically sealing a predetermined quantity of a sterilization sensitive agent within a reservoir provided in a rod;
    rigidly fastening said rod to an end of said container whereby said rod extends interiorly of said container and rigidly positions and maintains said reservoir within the slowest heating zone in the container;
    conventionally filling and sealing said container;
    subjecting said container to said sterilization cycle; and
    analyzing said sterilization sensitive agent to determine the effects of the sterilization process thereon.

7. The method as defined in claim 6 wherein said sterilization sensitive agent comprises viable bacteria in a liquid suspending menstrum.

8. The method as defined in claim 6 where in said sterilization sensitive agent comprises a sterilization sensitive chemical compound such as thiamine hydrochloride in a liquid suspending medium.

9. The method as in claim 7 wherein said analyzing step includes the steps of graphically determining the sterilization value from the number of surviving microorganisms remaining after the sterilization process.

10. The method as defined in claim 8 wherein said fastening step includes the step of:
    rigidly attaching a threaded fitting to said end of said container; and
    coupling said rod to said fitting.

* * * * *